(12) United States Patent
Satou et al.

(10) Patent No.: US 6,468,199 B1
(45) Date of Patent: Oct. 22, 2002

(54) MAGNETIC RESONANCE MEDICAL TREATMENT DEVICE AND MAGNETISM VARIATION CONTROL METHOD

(76) Inventors: Kiyoshi Satou, 12, Fukushima, 4-Chome, Yatuomachi Nei-Gun Toyama (JP), 939-2376; Kazuhito Sakano, 42, Kamishoumachi, Toyama-Shi Toyama (JP), 930-0826

(*) Notice: Subject to any disclaimer, the term of this patent is extended or adjusted under 35 U.S.C. 154(b) by 0 days.

(21) Appl. No.: 09/647,073
(22) PCT Filed: Nov. 20, 1998
(86) PCT No.: PCT/JP98/05250
  § 371 (c)(1),
  (2), (4) Date: Sep. 26, 2000
(87) PCT Pub. No.: WO00/30713
  PCT Pub. Date: Jun. 2, 2000
(51) Int. Cl.[7] .............................. A61N 2/00; A61B 17/52
(52) U.S. Cl. ........................................................... 600/9
(58) Field of Search ........................................ 600/9–15

(56) References Cited
FOREIGN PATENT DOCUMENTS

| JP | 5-237197 | * | 9/1993 |
| JP | 7-163631 | * | 6/1995 |
| JP | 8-57063 | * | 3/1996 |
| JP | 8-252331 | * | 10/1996 |

* cited by examiner

Primary Examiner—John P. Lacyk
(74) Attorney, Agent, or Firm—Michaelson & Wallace; Peter L. Michaelson

(57) ABSTRACT

The present invention relates to a magnetic resonance medical treatment device for applying magnetism to the body of a patient to thereby treat decease or improve the patient's health condition. The invention also relates to a method for magnetism variation control adapted to control magnetism generated by a magnetism generator such as the magnetic resonance medical treatment device. In order to enable diversified magnetic medical treatments, a magnetic resonance medical treatment device according to the present invention includes a director which contains two magnetism generators—which each include a bar core and a conductor wound on the bar core—and a magnetism regulator connected to the director and adapted to individually regulate the intensities and directions of magnetic forces generated by the magnetism generators. A method for magnetism variation control according to the present invention causes one magnetism generator to resonate with the other magnetism generator.

17 Claims, 9 Drawing Sheets

MAGNETIC RESONANCE MEDICAL TREATMENT DEVICE AND MAGNETISM VARIATION CONTROL METHOD

TECHNICAL FIELD

The present invention relates to a magnetic resonance medical treatment device for applying magnetism to the body of a patient to thereby treat a disease or improve the patient's health condition. The invention also relates to a method for magnetism variation control adapted to control magnetism generated by a magnetism generator such as the magnetic resonance medical treatment device.

BACKGROUND ART

Generally, low-frequency medical treatment device, infrared medical treatment device, and magnetic medical treatment device are available as medical treatment device for easing or medically treating bodily disorders, such as stiff shoulders or lower back pain, through application of external stimulus to the body.

Among these apparatus, low-frequency medical treatment device and infrared medical treatment device may involve a bodily shock caused by application of electricity or heat during medical treatment, as well as the inconvenience of removing clothing for provision of treatment, since, for example, an electrode having a cord must be applied directly to an affected part of the body.

By contrast, in recent years, magnetic medical treatment device employing a permanent magnet, such as magnetic bands or magnetic stomach bands, have come into frequent use, since they do not involve a bodily shock as mentioned above and enable provision of treatment with no need for removing clothing. Also, a medical treatment performed through affixing of a small permanent magnet on an affected part of the body is well known.

Such magnetic medical treatment device employing a permanent magnet usually cannot vary the intensity of a magnetic force. Conventionally, therefore, clinical facilities use clinical magnetic medical treatment device in which the intensity of a magnetic force is varied; for example, through periodical alternation of the N-pole and the S-pole of a probe effected by periodically reversing current which flows to the coil of a magnetism generator contained in the probe.

Meanwhile, the applicant of the present invention has proposed a magnetic medical treatment device as disclosed in Japanese Patent Application Laid-Open (kokai) No. 8-252331. As shown in FIGS. 8 and 9, the magnetic medical treatment device includes an N-probe 5, an S-probe 6, and a control unit 7 which controls magnetism generated by the N-probe 5 and S-probe 6. The N-probe 5 and the S-probe 6 each include magnetism-generating means 3—which includes a bar core 1 of, for example, iron and a conductor 2 wound on the bar core 1—and a frame 4 of, for example, synthetic resin adapted to contain the magnetism-generating means 3.

The direction of winding the conductor 2 of the magnetism-generating means 3 is reversed between the N-probe 5 and the S-probe 6. A tip portion of the N-probe 5 is magnetized to the N-pole, whereas a tip portion of the S-probe 6 is magnetized to the S-pole.

The N-probe 5 and the S-probe 6 each have a pointed pressing portion 8, which is a portion of the core 1 having an overall conical shape and projecting from the tip portion thereof. The pointed pressing portion 8 is adapted to press, for example, an effective point of the body. The N-probe 5 and the S-probe 6 are connected to the control unit 7 through spiral cords 9 and pin jacks 10.

The control unit 7 includes magnetism regulation means for regulating the intensity of magnetism generated by the N-probe 5 and the S-probe 6, switching means for varying the period with which magnetism is generated in the form of pulses, and duty ratio regulation means for varying the duty ratio of pulsed magnetism, whereby diversified pulse currents (including a direct current) can be supplied.

The thus-configured magnetic medical treatment device of Japanese Patent Application Laid-Open (kokai) No. 8-252331 is used, for example, in the following modes: the distance between the body skin and the probes is varied; the distance between the N-probe 5 and the S-probe 6 is varied while the probes are positioned in the vicinity of the body; the intensity of magnetism, frequency, and duty ratio of at least either the N-probe 5 or the S-probe 6 are varied while the N-probe 5 and the S-probe 6 are applied to predetermined positions; and the pointed pressing portions 8 are applied to effective points of the body so as to stimulate the points.

As described above, through regulation of the intensity of the magnetic forces generated by the N-probe 5 and the S-probe 6, the magnetic medical treatment device of Japanese Patent Application Laid-Open (kokai) No. 8-252331 complements magnetic balance within the body or, on the contrary, intentionally disturbs magnetic balance within the body so as to induce the balancing capability of a human being. Such medical treatment can be effectively carried out in addition to a conventional treatment. Further, weak current can be caused to flow within the body to thereby activate neural functions. Also, in addition to electromagnetic force, electromagnetic induction, and electrodynamic force, optimum pulsed magnetism produces a massaging effect, so that blood circulation is promoted. Further, through appropriate stimulation of effective points of the body or muscles by means of the pointed pressing portions, bodily stiffness can be eased.

However, the magnetic medical treatment device of Japanese Patent Application Laid-Open (kokai) No. 8-252331 leaves room for further improvement of control means for varying magnetism applied to the body.

In view of the foregoing, the applicant of the present invention has achieved the present invention, and an object of the invention is to provide a magnetic medical treatment device capable of effecting diversified magnetic medical treatments, such as diversified variation of magnetic balance within the body through more diversified variation of magnetism applied to the body, or activation of neural functions through promotion of flow of weak current within the body.

Another object of the present invention is to provide a method for magnetism variation control in order to control diversified magnetism generated by a magnetism generator such as the magnetic medical treatment device.

DISCLOSURE OF THE INVENTION

In order to achieve the above objects, according to a first aspect of the present invention, there is provided a magnetic resonance medical treatment device characterized by comprising a director which contains two magnetism generators, each comprising a bar core and a conductor wound on the bar core, and a magnetism regulator connected to the director and adapted to individually regulate the intensities and directions of magnetic forces generated by the magnetism generators.

Through employment of the above configuration, the two magnetism generators fixedly contained in the director can be resonated, for example, by applying current to the conductors such that a core tip portion of one magnetism generator is magnetized to the N-pole, while a core tip portion of the other magnetism generator is periodically alternatingly magnetized to the N-pole and the S-pole (phase alternation). Accordingly, diversified magnetic medical treatments are enabled. Also, since variation of a magnetic field effected by resonance of the two magnetism generators can be superposed on variation of intensity of magnetic forces generated by the two magnetism generators, magnetic medical treatments which can be practiced are further diversified to include those which utilize a three-dimensional magnetism variation.

In order to achieve the above objects, according to a second aspect of the present invention, there is provided a magnetic resonance medical treatment device according to the first aspect, characterized in that, of the two magnetism generators, one magnetism generator has a core in a cylindrical shape, and the other magnetism generator is disposed within a hollow portion of the core.

Through employment of the above configuration, a magnetic field generated by the two magnetism generators can be varied, since one magnetism generator of a cylindrical shape and the other magnetism generator can be resonated.

Accordingly, diversified magnetic medical treatments are enabled. Also, since variation of a magnetic field effected by resonance of the two magnetism generators can be superposed on variation of intensity of magnetic forces generated by the two magnetism generators, magnetic medical treatments which can be practiced are further diversified to include those which utilize a three-dimensional magnetism variation.

In order to achieve the above objects, according to a third aspect of the present invention, there is provided a magnetic resonance medical treatment device according to the first or second aspect, characterized in that the two magnetism generators are disposed such that core tip portions thereof are located a small distance apart from each other.

Through employment of the above configuration, a magnetic field generated by the two magnetism generators can be varied, since the core tip portions of the two magnetism generators contained in the director can be resonated. Accordingly, diversified magnetic medical treatments are enabled. Also, since variation of a magnetic field effected by resonance of the two magnetism generators can be superposed on variation of intensity of magnetic forces generated by the two magnetism generators, magnetic medical treatments which can be practiced are further diversified to include those which utilize a three-dimensional magnetism variation.

In order to achieve the above objects, according to a fourth aspect of the present invention, there is provided a magnetic resonance medical treatment device characterized by comprising a director which contains a plurality of magnetism generators—which are arranged annularly and each comprise a bar core and a conductor wound on the bar core—and a magnetism regulator connected to the director and adapted to individually regulate the intensities and directions of magnetic forces generated by the magnetism generators.

Through employment of the above configuration, for example, rotary fluctuations can be imparted to magnetism that penetrates into the body, by sequentially changing the intensity of magnetic forces generated by the magnetism generators, which are annularly arranged within the director. Accordingly, diversified magnetic medical treatments are enabled.

In order to achieve the above objects, according to a fifth aspect of the present invention, there is provided a magnetic resonance medical treatment device according to any one of the first to fourth aspects, characterized in that a permanent magnet is disposed in the vicinity of the core tip portions of the two magnetism generators.

Through employment of the above configuration, even the magnetic force of the permanent magnet can be varied by application of the permanent magnet to an affected part of the body. Accordingly, coupled with magnetic medical treatments which utilize variation of a magnetic field effected by resonance of the two magnetism generators and variation of intensity of magnetic forces generated by the two magnetism generators, magnetic medical treatments which can be practiced are further diversified.

In order to achieve the above objects, according to a sixth aspect of the present invention, there is provided a magnet holder characterized by integrally holding core tip portions of the two magnetism generators of the magnetic resonance medical treatment device according to the first aspect and a permanent magnet disposed in the vicinity of the core tip portions.

Through use of the magnet holder, the permanent magnet to be applied to an affected part of the body can be fixed in the vicinity of the core tip portions; thus, diversified magnetic medical treatments are enabled without the permanent magnet being affixed on the affected part of the body.

In order to achieve the above objects, according to a seventh aspect of the present invention, there is provided a magnetic resonance medical treatment device characterized by comprising: a director which contains two magnetism generators, each comprising a bar core and a conductor wound on the bar core; a magnetism regulator connected to the director and adapted to individually regulate the intensities and directions of magnetic forces generated by the magnetism generators; and a magnet holder for integrally holding core tip portions and a permanent magnet disposed in the vicinity of the core tip portions.

Through employment of the above configuration, the permanent magnet to be applied to an affected part of the body can be fixed in the vicinity of the core tip portions, and the two magnetism generators contained in the director can be resonated, whereby the magnetic force of the permanent magnet and a magnetic field generated by the two magnetism generators can be varied. Accordingly, diversified magnetic medical treatments are enabled. Also, coupled with magnetic medical treatments which utilize variation of a magnetic field effected by resonance of the two magnetism generators and variation of intensity of magnetic forces generated by the two magnetism generators, magnetic medical treatments which can be practiced are further diversified.

In order to achieve the above objects, according to eighth and ninth aspects of the present invention, there are respectively provided a magnet holder according to the sixth aspect and a magnetic resonance medical treatment device according to the seventh aspect, characterized in that the magnet holder is made of an elastic material. Examples of the elastic material include a resin having elasticity, such as rubber.

Through employment of the above configuration, the elastic magnet holder can absorb micro-vibrations of the two resonating magnetism generators; thus, the permanent magnet to be applied to an affected part of the body can be easily fixed in the vicinity of the core tip portions. Also, when the magnet holder is made of a resin, safety to the human body is ensured.

In order to achieve the above objects, according to tenth and eleventh aspects of the present invention, there are respectively provided a magnet holder according to the sixth aspect and a magnetic resonance medical treatment device according to the seventh aspect, characterized in that the magnet holder is made of a non-magnetic material. Examples of the non-magnetic material include an aluminum alloy and a resin.

Through employment of the above configuration, the magnet holder can be easily attached to or detached from the core tip portions, and the permanent magnet can be easily attached to or detached from the magnet holder. Further, when used as material for the magnet holder, an aluminum alloy improves the ornamental effect of the magnet holder.

In order to achieve the above objects, according to a twelfth aspect of the present invention, there is provided a method for magnetism variation control, characterized in that one magnetism generator is caused to resonate with the other magnetism generator.

Through employment of the method for magnetism variation control through resonance according to the present invention, a magnetic medical treatment device can, for example, apply to the body magnetic variation effected in the same direction as the resonance direction of the magnetism generators, thereby enabling diversified magnetic medical treatments to be practiced according to a patient's symptoms.

In order to achieve the above objects, according to a thirteenth aspect of the present invention, there is provided a method for magnetism variation control according to the twelfth aspect, characterized in that the frequency of the resonance is changed in accordance with a 1/f fluctuation.

A 1/f fluctuation is generally known as a period for bringing peace of mind or a sense of security to humans. For example, classical music, a gentle breeze, and the sound of waves at the water's edge involve 1/f fluctuations. Also, in the human body, a brain wave (α wave) arising during meditation or a cardiac cycle during a resting period is known to follow 1/f fluctuations.

Accordingly, by changing the frequency of the aforementioned resonance in accordance with a 1/f fluctuation, a magnetic medical treatment device can, for example, apply to the body magnetism which varies in accordance with a 1/f fluctuation in the same direction as the resonance direction of magnetism generators. Accordingly, natural, comfortable magnetic variation suitable to human physiology can be applied to a patient; particularly, 1/f fluctuations are induced in blood circulation.

In order to achieve the above objects, according to a fourteenth aspect of the present invention, there is provided a method for magnetism variation control, characterized in that the intensity of a magnetic force generated by a magnetism generator is varied in accordance with a 1/f fluctuation.

Through employment of the method for magnetism variation control according to the present invention, a magnetic medical treatment device can, for example, apply to the body magnetism which varies in accordance with a 1/f fluctuation in the same direction as that in which a magnetic force generated by a magnetism generator varies; i.e., a direction in which magnetic flux density varies. Thus, the depth of penetration of magnetism into the body can be varied in accordance with a 1/f fluctuation. Accordingly, natural, comfortable magnetic variation suitable to human physiology can be applied to a patient; particularly, 1/f fluctuations are induced in blood circulation.

Notably, through superposition of magnetism which varies in accordance with a 1/f fluctuation in the same direction as the resonance direction of magnetism generators, on magnetism which varies in accordance with a 1/f fluctuation in the same direction as that in which the magnetic flux density varies, magnetic variation applied to a patient can be further diversified.

In order to achieve the above objects, according to a fifteenth aspect of the present invention, there is provided a method for magnetism variation control, characterized in that variation of a magnetic field effected by resonance of two or more magnetism generators is superposed on variation of intensity of magnetic forces generated by the two or more magnetism generators.

Through employment of the method for magnetism variation control according to the present invention, in which variation of a magnetic field effected by resonance of two or more magnetism generators is superposed on variation of intensity of magnetic forces generated by the two or more magnetism generators, a magnetic medical treatment device can, for example, apply to the body a complicated magnetic variation. Thus, magnetic medical treatments which can be practiced according to a patient's symptoms are further diversified to include magnetic medical treatments which utilize a three-dimensional magnetism variation.

In order to achieve the above objects, according to a sixteenth aspect of the present invention, there is provided a magnetism resonator-generator characterized by comprising a plurality of magnetism generators arranged adjacent to one another and a control unit for controlling a resonant frequency of resonant magnetism generated by the magnetism generators.

Through employment of the above configuration, a magnetic medical treatment device can, for example, apply to the body magnetic variation in the same direction as the resonance direction of the magnetism generators, thereby enabling diversified magnetic medical treatments to be practiced according to a patient's symptoms.

In order to achieve the above objects, according to a seventeenth aspect of the present invention, there is provided a magnetism resonator-generator according to the sixteenth aspect, characterized in that the frequency of the resonance is changed in accordance with a 1/f fluctuation.

Through employment of the above configuration, a magnetic medical treatment device can, for example, apply to the body magnetism which varies in accordance with a 1/f fluctuation in the same direction as the resonance direction of magnetism generators. Accordingly, natural, comfortable magnetic variation suitable to human physiology can be applied to a patient; particularly, 1/f fluctuations are induced in blood circulation.

Figure 1:
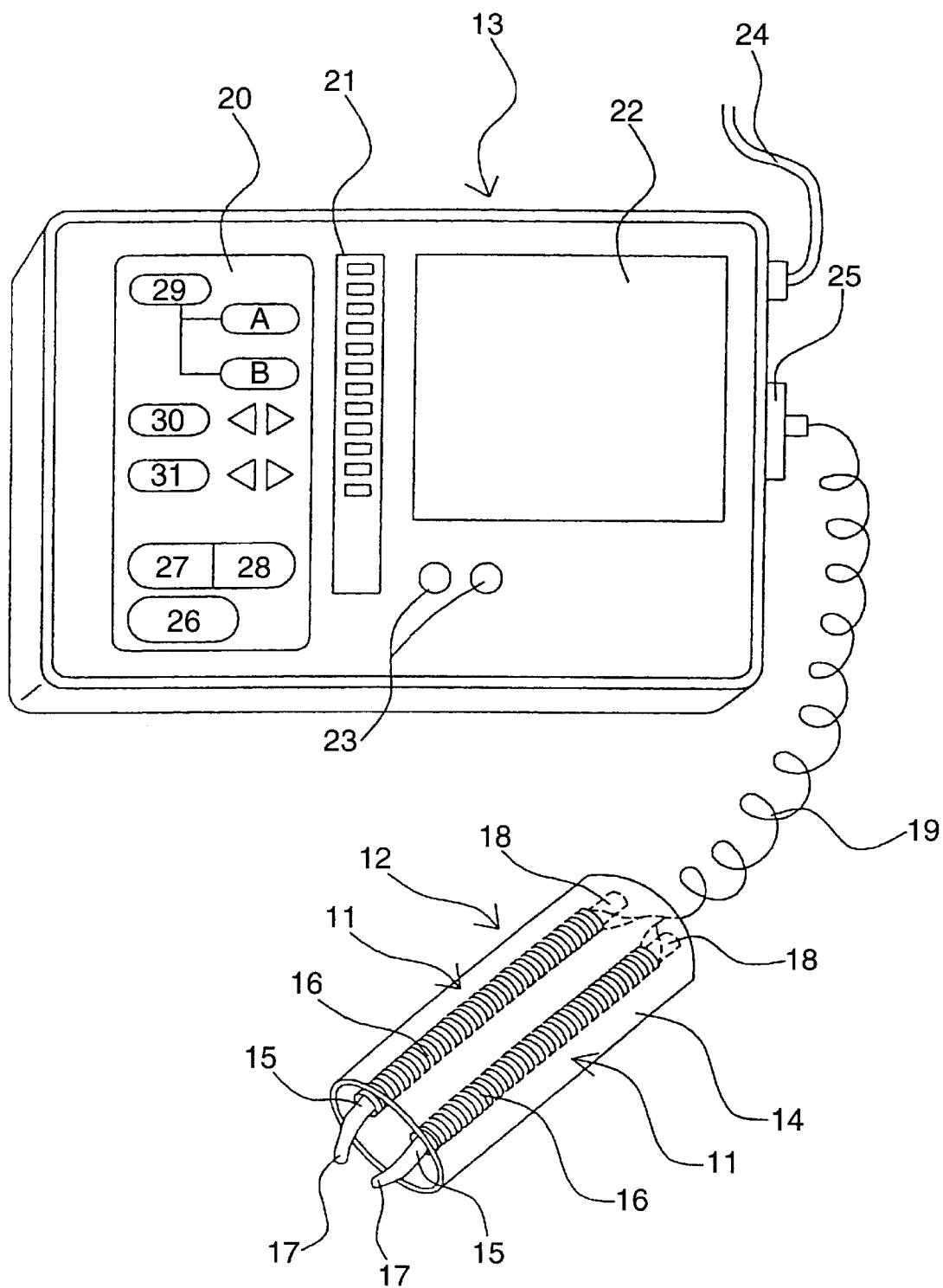
FIG. 1 is a perspective view showing a magnetic resonance medical treatment device according to the present invention.

DESCRIPTION OF SYMBOLS 11 magnetism generator
12 director
13 control unit
15 core
17 tip portion
20 sheet switch panel
21 magnetic-output display unit
22 liquid-crystal display unit
33 microcomputer
34 frequency change circuit
35 phase change circuit
36 duty ratio regulation circuit
42 magnet holder

BEST MODE FOR CARRYING OUT THE INVENTION

An embodiment of the present invention will be scribed with reference to the drawings.

Figure 2:
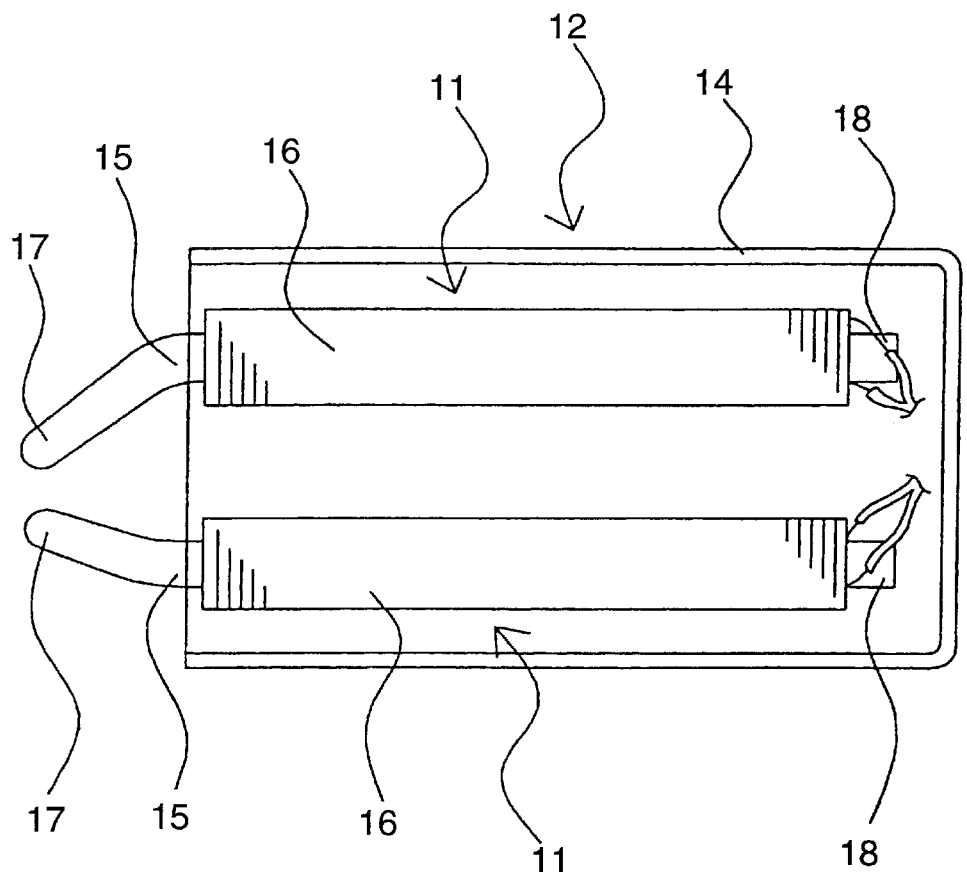
FIG. 2 is a sectional view showing a director of the magnetic resonance medical treatment device according to the present invention.

As shown in FIGS. 1 and 2, a magnetic resonance medical treatment device according to the embodiment of the present invention includes a director 12 which contains magnetism generators 11 and which the user holds in his/her hand and applies to an affected part of the body, and a control unit 13 for controlling magnetism generated by the director 12.

As shown in FIG. 2, the director 12 includes a cylindrical frame 14 made of, for example, a synthetic resin, and the magnetism generators 11, which each includes a bar core 15 made of, for example, iron and a conductor 16 wound on the core 15. As shown in FIG. 1, one end of the cylindrical frame 14 is opened, and bent end portions 17 of the cores 15 are projected out through the opening portion. The two magnetism generators 11 are fixedly disposed within the frame 14 such that the respective cores 15 are in parallel to each other. Since the magnetism generators 11 are fixed to the frame 14 at other end portions 18 of the cores 15, the tip portions 17 of the cores 15 can finely vibrate, which will be described later.

The director 12 is connected to the control unit 13 through a spiral cord 19.

As shown FIG. 1, the control unit 13 includes a sheet switch panel 20, a magnetic-output display unit 21 for displaying a magnetic output, a liquid-crystal display unit 22 for displaying, for example, time, and indicator lamps 23 for indicating power ON/OFF and an operational state, which are all provided on the top surface thereof. The control unit 13 further includes a power cord 24 and a director connector 25 for connection to the director 12, which are provided on a side surface thereof.

The sheet switch panel 20 includes a power switch 26, a start switch 27, a stop switch 28, a mode selector switch 29, a magnetic-output regulation switch 30, and a timer switch 31. By use of these switches, the user transmits an instruction to the control unit 13. The magnetic-output display unit 21 enables the user to visually recognize varying magnetism during medical treatment, by means of a bar LED. The liquid-crystal display unit 22 displays, for example, the rest of treating time and a waveform indicative of a varying magnetic output. The indicator lamps 23 are lit in an interlocking relation with the power switch 26, the start switch 27, and the stop switch 28.

Figure 3:
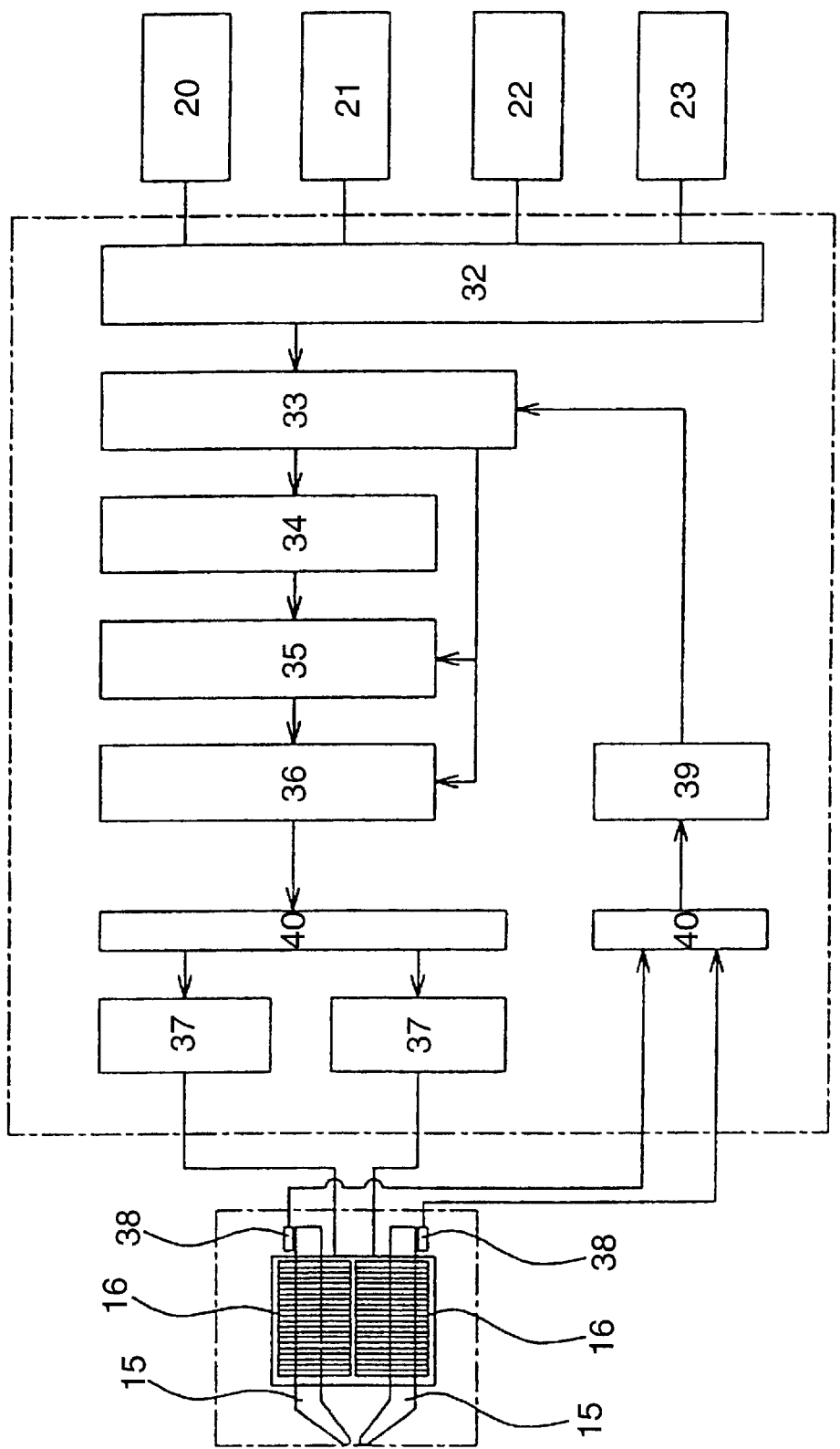
FIG. 3 is a block diagram showing an internal controller of the magnetic resonance medical treatment device according to the present invention.

Next, an internal controller of the control unit 13 and an instruction transmission mechanism for transmission of an instruction from the user to the controller will be described with reference to the block diagram of FIG. 3.

The internal controller of the control unit 13 includes an input/output circuit 32 connected to the sheet switch panel 20, the magnetic-output display unit 21, the liquid-crystal display unit 22, and the indicator lamps 23 provided on the top surface of the control unit 13; a microcomputer 33 connected to the input/output circuit 32 and adapted to control the entire internal controller; a frequency change circuit 34, a phase change circuit 35, and a duty ratio regulation circuit 36, which are connected to the microcomputer 33 and are adapted to regulate a magnetic output; drive ICs 37 connected to the respective conductors 16 (coils) contained in the director 12; and an input circuit 39 connected to thermal protectors 38 attached to the respective cores 15 contained in the director 12.

The input/output circuit 32 transmits instructions from the power switch 26, the start switch 27, the stop switch 28, the mode selector switch 29, the magnetic-output regulation switch 30, and the timer switch 31—which are all provided on the sheet switch panel 20—to the microcomputer 33 in the form of signals.

The microcomputer 33 processes signals received from the input/output circuit 32 and the input circuit 39 according to programs and sends instruction signals to the frequency change circuit 34, the phase change circuit 35, and the duty ratio regulation circuit 36.

The frequency change circuit 34 operates according to a program contained in the microcomputer 33 so as to control the frequency of magnetism generated by the director 12 through regulation of the current applied to the conductors 16. The phase change circuit 35 operates according to the program contained in the microcomputer 33 so as to vary the direction of current applied to the conductors 16. Through varying of the direction of current applied to the conductors 16, current may be applied to the conductors 16, for example, such that the core tip portion 17 of one magnetism generator 11 is magnetized to the N-pole, while the core tip portion 17 of the other magnetism generator 11 is periodically alternatingly magnetized to the N-pole and the S-pole (phase alternation), whereby the two magnetism generators 11 contained in the director 16 can be resonated. The duty ratio regulation circuit 36 operates according to the program contained in the microcomputer 33 so as to regulate the duty ratio of magnetism generated by the director 12.

The drive ICs 37 transmit to the conductors 16 signals from the frequency change circuit 34, the phase change circuit 35, and the duty ratio regulation circuit 36. A photocoupler 40 is disposed between the drive ICs 37 and the frequency change circuit 34, the phase change circuit 35, and the duty ratio regulation circuit 36. Generally, when current to be applied to a coil is turned ON or when current applied to a coil is turned OFF, large noise is generated due to an induced electromotive force, potentially causing a malfunction in an electronic device, such as a microcomputer. According to the present embodiment, the photocoupler 40 is provided in order to optically cut off a signal passage, thereby preventing entry of noise.

The input circuit 39 transmits a signal from the thermal protectors 38 to the microcomputer 33. The photocoupler 40 is also disposed between the thermal protectors 38 and the input circuit 39 in order to prevent entry of noise.

As described above, the thermal protector 38 is attached to each of the cores 15 contained in the director 12, thereby preventing excessive heat generation of a coil when current is applied to the coil. S-pecifically, when the thermal protector 38 reaches a set temperature, a signal is transmitted from the input circuit 39 to the microcomputer 33 so as to cut off current which flows to the coil. Thus, the tip portions 17 of the core 15, which is brought close to an affected part of the body, can be held at a safe temperature.

The thus-configured magnetic resonance medical treatment device according to the present embodiment is used in the following manner.

In order to use the magnetic resonance medical treatment device according to the present embodiment, first, the power switch 26 on the sheet switch panel 20 is turned on. While the liquid-crystal display unit 22 and the magnetic-output display unit 21 are being observed, the optimum setting is established by appropriate use of the mode selector switch 29, the magnetic-output regulation switch 30, and the timer switch 31.

Next, the tip portions 17 of the cores 15 of the director 12 are applied to an affected part of the body, and the start switch 27 is pressed to start a medical treatment. During treatment, there can be regulated a magnetic field induced through resonance of the tip portions 17 of the cores 15 and a magnetic force generated by the cores 15, by appropriate use of the mode selector switch 29 and the magnetic-output regulation switch 30.

Figure 4:
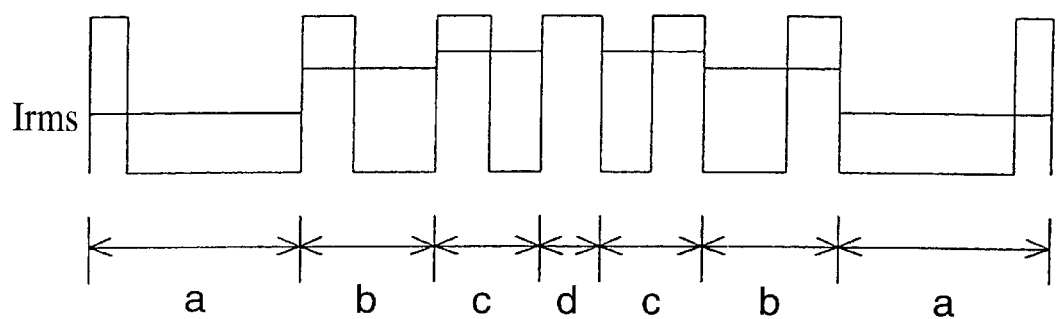
FIG. 4 is a time chart showing a pulse signal emitted from the magnetic resonance medical treatment device according to the present invention while the apparatus is in operation.

Modes which the user can select by use of the mode selector switch 29 shown in FIG. 1 will be described below. As shown in FIG. 4, "mode A" uses a pulse signal generated in the following manner: the period is varied in the order of a, b, c, d, c, b, and a, and this variation of period is superposed on variation of duty ratio. According to the "mode A," effective current value $I_{rms}$ varies gently as shown in FIG. 4, so that a magnetic force generated by the core 15 follows a "beat" wave motion that involves gentle variations. Notably, when the period and the duty ratio vary in accordance with a 1/f fluctuation, magnetism applied to the body can be varied in accordance with a 1/f fluctuation in the same direction as that in which the magnetic force varies; i.e., a direction in which the magnetic flux density varies. Thus, the depth of penetration of magnetism into the body can be varied in accordance with a 1/f fluctuation. Accordingly, natural, comfortable magnetic variation suitable to human physiology can be applied to a patient; particularly, 1/f fluctuations are induced in blood circulation.

"Mode B" is a mode in which variation of a magnetic field effected by resonance of the tip portions 17 of the cores 15 is further superposed on the above-described "mode A." When a magnetic field effected by resonance of the tip portions 17 of the cores 15 varies in accordance with a 1/f fluctuation, magnetism applied to the body varies in accordance with the 1/f fluctuation in the same direction as the resonance direction. Accordingly, natural, comfortable magnetic variation suitable to human physiology can be applied to a patient; particularly, 1/f fluctuations are induced in blood circulation. Therefore, more comfortable magnetic variation can be applied to a patient.

As described above, the magnetic resonance medical treatment device according to the present embodiment can practice diversified magnetic medical treatments according to a patient's symptoms.

In addition to the above-described mode for using the magnetic resonance medical treatment device according to the present embodiment, the apparatus may be used, for example, in the following manner. A small permanent magnet is affixed on an affected part of the body, and the tip portions 17 of the cores 15 are brought close to the permanent magnet. In this mode of use, even the magnetic force of the permanent magnet can be varied, so that magnetic medical treatments which can be practiced are further diversified.

Figure 5:
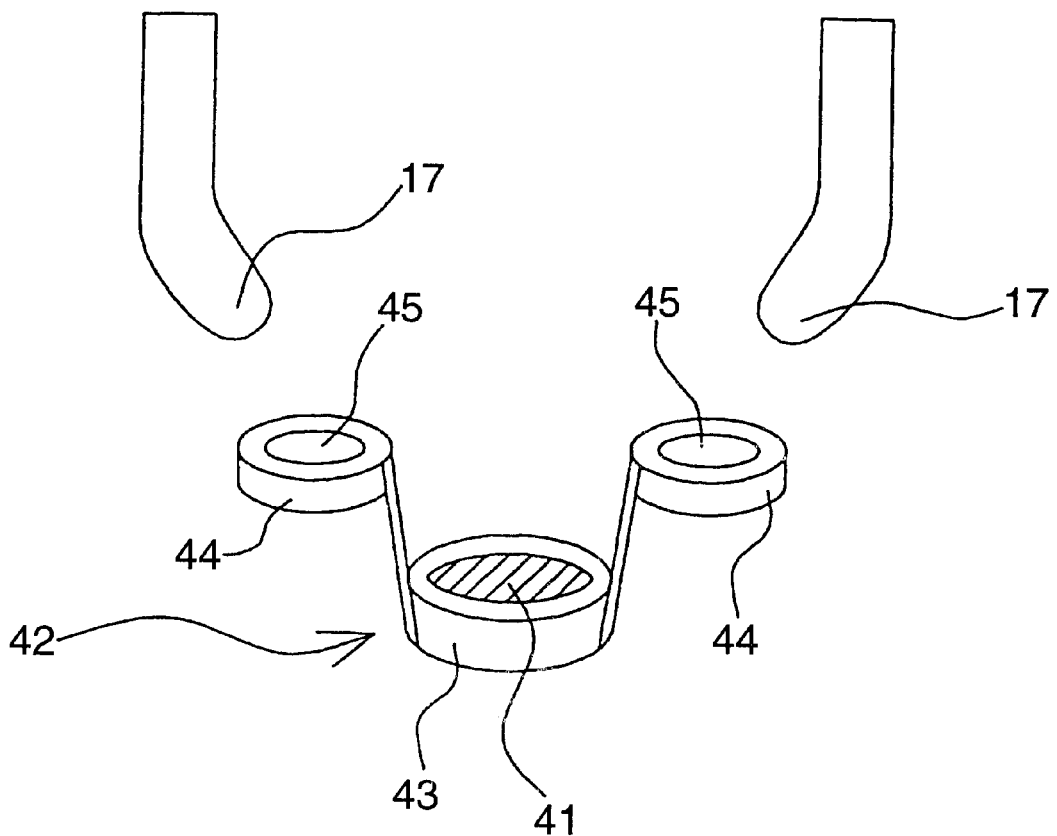
FIG. 5 is a perspective view showing a magnet holder according to the present invention.

FIG. 5 shows another mode for using the magnetic resonance medical treatment device in which a permanent magnet is utilized. As shown in FIG. 5, a magnet holder 42 is employed in order to integrally hold the tip portions 17 of the cores 15 and a permanent magnet 41. The magnet holder 42 includes a holder portion 43 for accommodating a permanent magnet, and attaching holder portions 44 located on both sides of the holder portion 43. The holder portion 43 and the attaching holder portions 44 are connected together. Preferably, a material for the magnet holder 42 is elastic as in the case of rubber and also non-magnetic. When a medical treatment is to be practiced, the permanent magnet 41 is loaded into the holder portion 43, and the tip portions 17 of the cores 15 are inserted into corresponding holes 45 formed in the attaching holder portions 44. Then, the permanent magnet 41 is brought close to an affected part of the body.

Through utilization of the magnet holder 42, there is no need for directly affixing the permanent magnet 41 on an affected part of the body, whereby a patient can effectively receive magnetic medical treatments without taking off clothing.

Figure 6:
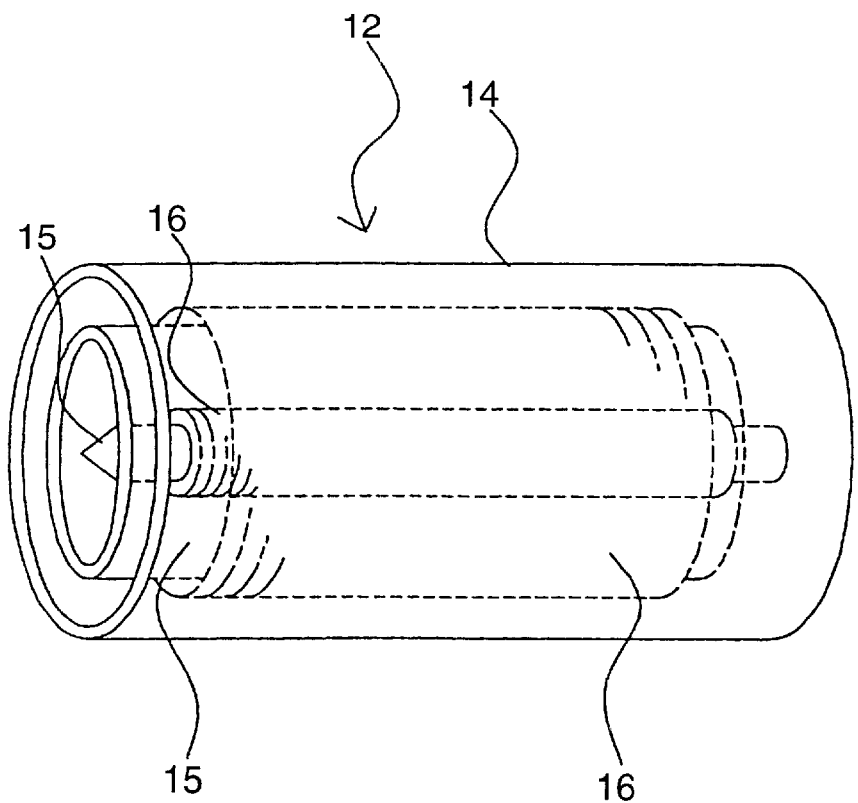
FIG. 6 is a perspective view and sectional view showing a director in another embodiment of a magnetic resonance medical treatment device according to the present invention.

The magnetic resonance medical treatment device according to the present embodiment may employ the director 12 which is configured as shown in FIG. 6. Of the two magnetism generators 11 contained in the director 12, one magnetism generator 11 has the core 15 in a cylindrical shape, and the other magnetism generator 11 is disposed within the hollow portion of the core 15.

By use of the cylindrical core 15, the cores 15 can provide diversified modes of resonance, thereby enabling further diversified magnetic medical treatments.

Figure 7:
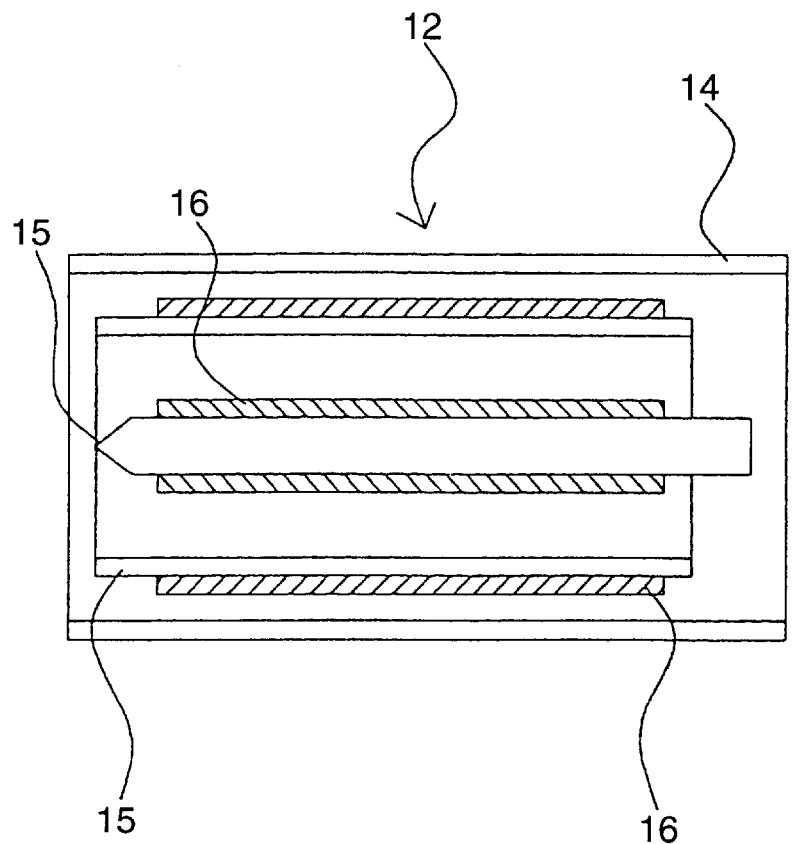
FIG. 7 is a perspective view showing a director in still another embodiment of a magnetic resonance medical treatment device according to the present invention.
Figure 8:
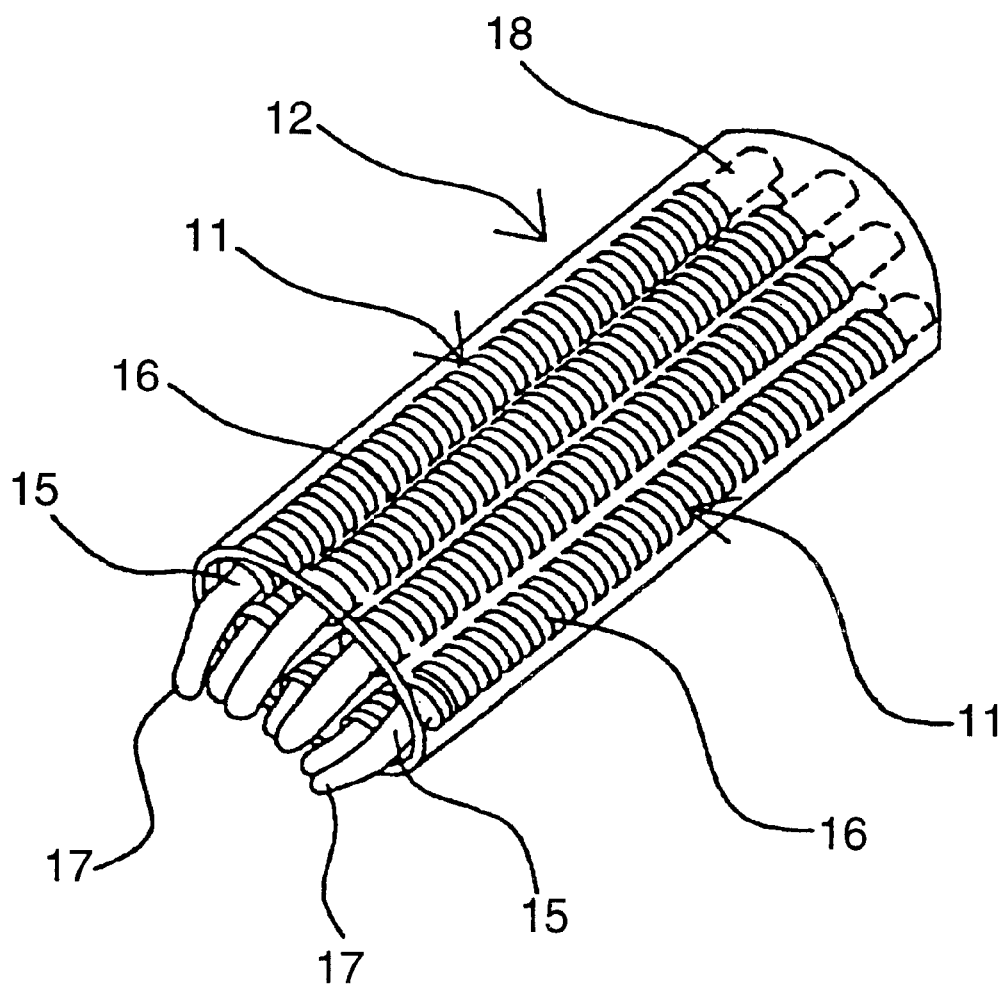
FIGS. 8 and 9 is a perspective view showing a conventional magnetic resonance medical treatment device.
Figure 9:
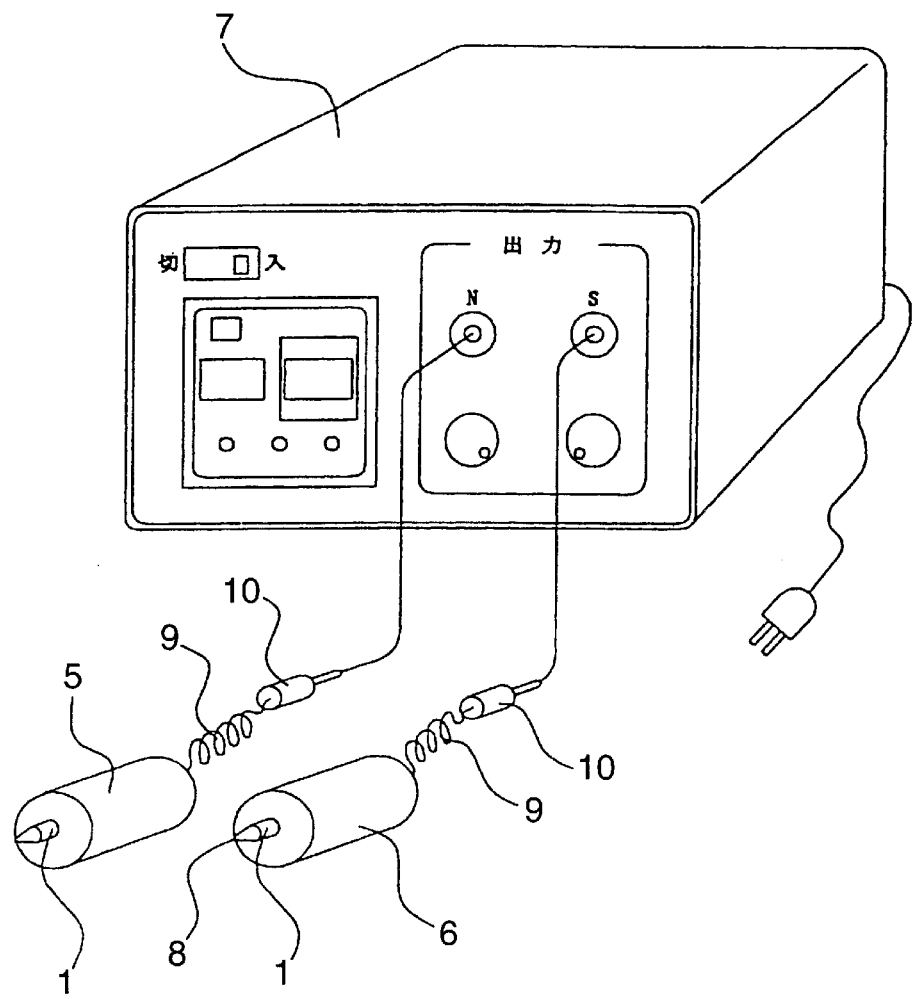
Figure 10:
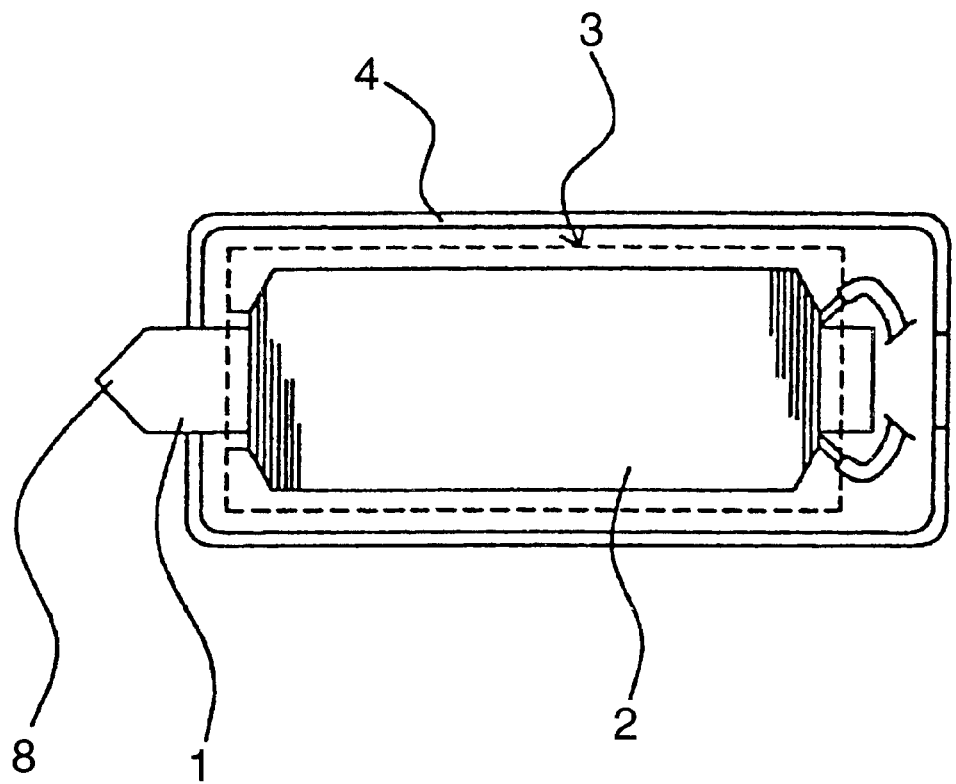
FIG. 10 is a sectional view showing a probe of the conventional magnetic resonance medical treatment device.

Further, the magnetic resonance medical treatment device according to the present embodiment may employ the director 12 which is configured as shown in FIG. 7. A plurality of magnetism generators 11 is annually disposed within the director 12.

Through employment of the above configuration, spirally rotary fluctuations can, for example, be imparted to magnetism that penetrates into the body, by sequentially changing the intensity of magnetic forces generated by the magnetism generators 11. Accordingly, diversified magnetic medical treatments are enabled.

What is claimed is:

1. A magnetic resonance medical treatment device comprising a director which contains two magnetism generators, each comprising a bar core and a conductor wound on the bar core, and a magnetism regulator connected to the director and adapted to individually regulate the intensities and directions of magnetic forces generated by the magnetism generators.

2. A magnetic resonance medical treatment device according to claim 1, wherein one of said two magnetism generators has a core in a cylindrical shape, and the other of said two magnetism generators is disposed within a hollow portion of the core.

3. A magnetic resonance medical treatment device according to claim 1, wherein said two magnetism generators are disposed such that core tip portions thereof are located a small distance apart from each other.

4. A magnetic resonance medical treatment device comprising a director which contains a plurality of magnetism generators—which are arranged annularly and each comprise a bar core and a conductor wound on the bar core—and a magnetism regulator connected to the director and adapted to individually regulate the intensities and directions of magnetic forces generated by the magnetism generators.

5. A magnetic resonance medical treatment device according to claim 1, wherein a permanent magnet is disposed in the vicinity of the core tip portions of the two magnetism generators.

6. A magnet holder comprising integrally holding core tip portions of the two magnetism generators of the magnetic resonance medical treatment device according to claim 1 and a permanent magnet disposed in the vicinity of the core tip portions.

7. A magnetic resonance medical treatment device characterized by comprising: a director which contains two magnetism generators, each comprising a bar core and a conductor wound on the bar core; a magnetism regulator connected to the director and adapted to individually regulate the intensities and directions of magnetic forces generated by the magnetism generators; and a magnet holder for integrally holding core tip portions and a permanent magnet disposed in the vicinity of the core tip portions.

8. A magnet holder according to claim 6, wherein said magnet holder is made of an elastic material.

9. A magnetic resonance medical treatment device according to claim 7, wherein said magnet holder is made of an elastic material.

10. A magnet holder according to claim 6, wherein said magnet holder is made of a non-magnetic material.

11. A magnetic resonance medical treatment device according to claim 7, wherein said magnet holder is made of a non-magnetic material.

12. A method for magnetism variation control comprising, causing one magnetism generator to resonate with another magnetism generator.

13. A method for magnetism variation control according to claim 12, wherein the frequency of the resonance is changed in accordance with a 1/f fluctuation.

14. A method for magnetism variation control comprising, varying the intensity of a magnetic force generated by a magnetism generator in accordance with a 1/f fluctuation.

15. A method for magnetism variation control comprising, superposing variations of a magnetic field effected by resonance of two or more magnetism generators on variations of intensity of magnetic forces generated by the two or more magnetism generators.

16. A magnetism resonator-generator comprising a plurality of magnetism generators arranged adjacent to one another and a control unit for controlling a resonant frequency of resonant magnetism generated by the magnetism generators.

17. A magnetism resonator-generator according to claim 16, wherein the frequency of the resonance is changed in accordance with a 1/f fluctuation.

* * * * *